United States Patent [19]

Hardtmann et al.

[11] 4,451,448
[45] May 29, 1984

[54] 1-SUBSTITUTED TRICYCLIC QUINAZOLINONES USEFUL AS TRANQUILIZERS

[75] Inventors: Goetz E. Hardtmann, Morristown; William J. Houlihan, Mt. Lakes, both of N.J.

[73] Assignee: Sandoz, Inc., E. Hanover, N.J.

[21] Appl. No.: 427,281

[22] Filed: Sep. 29, 1982

Related U.S. Application Data

[63] Continuation-in-part of Ser. No. 401,647, Jul. 26, 1982, abandoned, which is a continuation-in-part of Ser. No. 302,484, Sep. 16, 1981, abandoned.

[51] Int. Cl.$^3$ .................. A61K 31/505; C07D 487/04
[52] U.S. Cl. ..................................... 424/251; 544/250
[58] Field of Search ........................ 544/250; 424/251

[56] References Cited

U.S. PATENT DOCUMENTS

| | | | |
|---|---|---|---|
| 3,598,823 | 8/1971 | Hardtmann | 544/250 |
| 3,887,559 | 6/1975 | Hardtmann | 544/250 |
| 3,905,976 | 9/1975 | Hardtmann | 544/250 |
| 3,963,720 | 6/1976 | Hardtmann | 544/247 |

Primary Examiner—Donald G. Daus
Assistant Examiner—Diana G. Rivers
Attorney, Agent, or Firm—Gerald D. Sharkin; Richard E. Vila

[57] ABSTRACT

Minor tranquilizers preparable by known processes are represented by the following structural formula I:

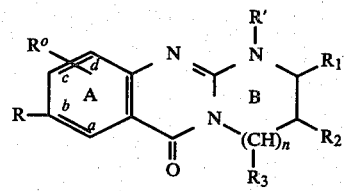

wherein
  $R^o$ is hydrogen, halo of atomic weight of from 18 to 80, i.e. fluoro, chloro or bromo or alkyl of 1 to 3 carbon atoms,
  R is halo of atomic weight of from 18 to 80, alkyl of 1 to 4 carbon atoms or trifluoromethyl,
  R' is alkenyl of 3 to 6 carbon atoms, alkynyl of 3 to 6 carbon atoms, cycloalkyl of 3 to 8 carbon atoms, norbornyl, alkyl of 1 to 3 carbon atoms substituted by cycloalkyl of 3 to 7 carbon atoms or —CH$_2$(F$_x$-ALK) wherein x is 1 to 3 and ALK is alkyl of 1 to 4 carbon atoms,
  $R_1$, $R_2$, and $R_3$ are independently hydrogen or alkyl of 1 or 2 carbon atoms, and
  n is 0 or 1.

29 Claims, No Drawings

1-SUBSTITUTED TRICYCLIC QUINAZOLINONES USEFUL AS TRANQUILIZERS

This is a continuation in part of application Ser. No. 401,647, filed July 26, 1982 which is a continuation-in-part of application Ser. No. 302,484 filed Sept. 16, 1981, now both abandoned.

The present invention relates to substituted tricyclic compounds which are quinazolinones, and also relates to methods and compositions for utilization of the compounds based on their biological activity.

The compounds of the invention may be represented by the following structural formula I:

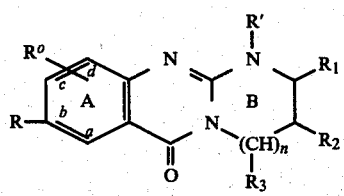

wherein
$R^o$ is hydrogen, halo of atomic weight of from 18 to 80, ie. fluoro, chloro or bromo, or alkyl of 1 to 3 carbon atoms,
R is halo of atomic weight of from 18 to 80, alkyl of 1 to 4 carbon atoms or trifluoromethyl,
R' is alkenyl of 3 to 6 carbon atoms, alkynyl of 3 to 6 carbon atoms, cycloalkyl of 3 to 8 carbon atoms, norbornyl, alkyl of 1 to 3 carbon atoms substituted by cycloalkyl of 3 to 7 carbon atoms or —CH$_2$(F$_x$ALK) wherein x is 1 to 3 and ALK is alkyl of 1 to 4 carbon atoms,
$R_1, R_2$, and $R_3$ are independently hydrogen or alkyl of 1 or 2 carbon atoms, and
n is 0 or 1.

The compounds of the formula I may be prepared in a process (a) by reacting a compound of the formula II

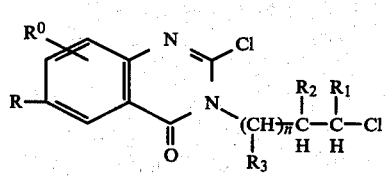

wherein $R^o$, R, $R_1$, $R_2$, $R_3$ and n are as above defined with a compound of the formula III:

R'—NH$_2$   III wherein R' is as defined.

The preparation of the compounds of the formula I in process (a) by reaction of compounds II and III may be suitably carried out temperatures of from 20° C. to 160° C., preferably 40° C. to 90° C. The reaction is conveniently carried out in the presence of an inert organic solvent such as dimethylacetamide or a lower alkanol, eg. ethanol. The resulting reaction product of the formula I may be recovered from the resulting reaction mixture by working up by established procedures.

The compounds of the formula I may also be prepared in a process (b) by reacting a compound of the formula IV:

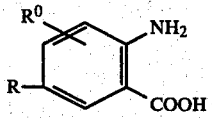

wherein $R^o$ and R are as defined, with a compound of the formula V:

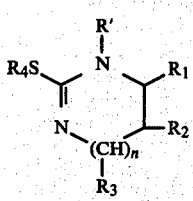

wherein R', $R_1$, $R_2$, $R_3$, and n and m are as defined and $R_4$ is alkyl of 1 to 4 carbon atoms or benzyl.

The preparation of compounds I in process (b) by the reaction of compounds IV and V may be suitably carried out at elevated temperatures typically in the range of from 100° C. to 190° C., preferably 140° C. to 180° C. The reaction is conveniently carried out in an inert organic solvent of conventional type, preferably a higher boiling organic solvent such as dimethylacetamide and dimethylformamide, more preferably dimethylacetamide. The reaction products of formula I may be recovered from the reaction mixture by working up by established procedures.

The compounds of the formula I may also be prepared in a process (c) by reacting a compound of the formula VI:

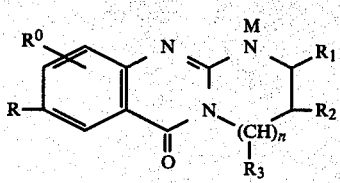

wherein $R^o$, R, $R_1$, $R_2$, $R_3$ and n are as defined and M is an alkali metal, with a compound of the formula VII:

X—R'   VII wherein R' is as defined and X is halo of atomic weight of from 35 to 130.

Process (c) is also of known type and may be effected as described in U.S. Pat. No. 3,598,823.

The compound of the formula I may further be prepared in a process (d) by reaction of a compound of the formula VIII:

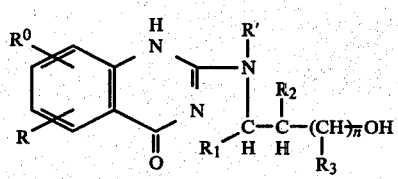

wherein $R^o$, R, R', $Y^o$, Y, $R_2$, $R_3$ and n are as defined, with a cyclizing agent, and treating the reaction product with an acid binding agent.

Process (d) may be effected under the conditions described for the analogous reaction in U.S. Pat. Nos. 3,887,559 and 3,905,976.

The intermediary reactants of the formulae II, III, IV, V, VI, VII and VIII are either known per se or may be prepared from known materials in accordance with procedures described in the literature.

The compounds of the formula I form acid addition salts which are included within the scope of the present invention. Those salts forming pharmaceutically acceptable salt forms, e.g. the hydrochloride, may of course be used pharmaceutically in accordance with the invention. The acid addition salts may be produced from the corresponding free bases by conventional procedures. Conversely, the free bases may be obtained from the salts by procedures known in the art.

The compounds of the formula I exhibit a Central Nervous System depressant effect in mammals and are useful as tranquilizers as indicated by the Flunitrazepam Receptor Binding Assay in accordance with the method basically described by R. C. Speth et al., *Life Science*, 22:859 (1978), and by the conflict segment of the well known Geller Conflict test in rats (1-20 mg./kg.) as described by J. Geller, Psychopharmacologia, Vol. 1, pages 482–492 (1960).

Routine and non-substantive modifications of the Flunitrazepam Receptor Binding Assay (hereinafter FBA TEST No. 1) that are evident from the following description are employed in such evaluation in which non-radioactive candidate compounds are tested for their ability to displace $^3$H-flunitrazepam binding from isolated calf brain benzodiazepine receptors. Hence, an aliquot of frozen calf caudate tissue is thawed and diluted with 0.5M Tris buffer containing metal ions (120 mM NaCl, 5 mM KCL, 2 mM $CaCl_2$ and 1 mM $MgCl_2$) to a final concentration of 8 mg/ml, i.e., a 25 fold dilution. This suspension is made homogenous by homogenation with a Brinkmann Polytron using a rheostat setting of 8 for 10 seconds. Ten $\lambda$ of $^3$H-flunitrazepam solution is diluted in 0.05M Tris buffer (pH 7.1 at 37° C.) to give a concentration of 10 nM ($3.13 \times 10^{-6}$ mg/ml). This solution is stored frozen at $-20°$ C., while the stock $^3$H-flunitrazepam solution in ethanol is kept refrigerated at $+2°$ C. Periodically, the stock ethanolic $^3$H-flunitrazepam solution is examined by TLC for chemical purity. If the purity becomes <90%, the stock solution is repurified or new high purity $^3$H-flunitrazepam is obtained and the impure $^3$H-flunitrazepam discarded. A 0.1 ml portion of 10 nM $^3$H-flunitrazepam "working" solution is added to $12 \times 75$ mm borosilicate disposable test tube along with 0.1 ml of freshly prepared 10% ethanol solution. This is the control tube for measuring total binding. Non-specific binding is determined by the addition of $2 \times 10^{-5}$M diazepam (in 10% ethanol) to other tubes in the place of 0.1 ml 10% ethanol. The specific binding is determined in the final results by subtraction of the non-specific binding from the total binding. All compounds screened have their results expressed in terms of specific binding and are tested at a final concentration of $1 \times 10^{-6}$M. Three mg of each compound are placed in $18 \times 150$ mm borosilicate disposable test tubes. These tubes are kept in the dark at room temperature until the day of the assay at which time 10 ml of absolute ethanol is added and the tubes placed in a Branson Ultrasonic Cleaner for 15 minutes and then vortexed in order to put the compounds into solution. All tubes are closely examined to make certain the compound is completely in solution. If not, then 3 drops of 2 N HCl is added. If the compound is still not in solution but a cloudy homogenous suspension is found, then the subsequent serial dilutions are continued. This gives a concentration of $\sim 1 \times 10^{-3}$M. The compounds are further diluted by serial dilution as follows: 0.1 ml of the $10^{-3}$M solution is added to 0.9 ml of 100% ethanol and vortexed. A 0.1 ml portion of this solution is added to 0.9 ml of water to give $\sim 1 \times 10^{-5}$M solution. A 0.1 ml portion of this solution is added to $12 \times 75$ mm test tubes for assay. All assays are run in duplicate. A 0.8 ml portion of caudate tissue suspension is added to all tubes, vortexed, incubated at 2° C. for 120 minutes, and rapidly filtered under vacuum through Whatman GF/G glass fiber filters. Each tube is rinsed once with 3 ml ice-cold 50 mM Tris buffer (pH 7.1 at 37° C.) and the filter subsequently washed once with 6 ml of the same Tris buffer. The $^3$H-flunitrazepam trapped on the filters is counted by liquid scintillation counting on a Beckman LS 8000 after the filters are rapidly shaken for 45 minutes in the scintillation vials with 10 ml of scintillation cocktail. Results of compounds screened are calculated by the on-line data reduction system in the Beckman LS 8000, and are expressed as a percent specifically bound compared to control.

Benzodiazepine receptors are obtained from male Holstein calves. Immediately after exsanguination, the brains are quickly removed and placed in ice. Dissection of the caudate nucleus is completed within 2 hours after sacrifice and the tissue weighed, and homogenized (1:10, W/V) in 0.05M Tris buffer (pH 7.1 at 37° C.) using a Brinkmann Polytron for 10 seconds with a rheostat setting of 8. The homogenate is centrifuged for 10 minutes at 20,000 RPM in a Sorvall RC2B centrifuge using a SS 34 head. The supernatant is decanted and the pellet washed twice to remove endogenous dopamine by resuspension with the use of the Brinkmann Polytron and recentrifugation. The final pellet is resuspended in 0.05M Tris (pH 7.1 at 37° C.) containing 120 mM NaCl, 5 mM KCl, 2 mM $CaCl_2$, and 1 mM $MgCl_2$ in a final concentration of 200 mg wet weight starting material/ml of buffer. The homogenate is stored in 4 ml aliquots in glass bottles in liquid nitrogen.

Substantially similar results are obtainable in a Flunitrazepam Receptor Binding Assay as described by Chang et. al., Eur. J. Pharmacol., 48, 213 (1978): when carried out with the non-substantive modifications evident from the following description (hereinafter FBA TEST No. 2): Fresh calf brain cortex is homogenized in a 19 fold volume of Tris-HCl buffer pH 7.4, using a Brinkman Polytron PT 20 and centrifuged at 50'000 g for 10 min. The pellets are frozen at $-20°$ C. and resuspended in a 400 fold volume of Tris-buffer pH 7.4 before use for the binding assay. The assay mixtures consist of 1.8 ml of homogenate (corresponding to 4.5 mg of original tissue), 0.1 ml [$^3$H]-Flunitrazepam (final concentration 1.5 nM), and 0.1 ml of buffer for determination of total binding or 0.1 ml of unlabelled Flunitrazepam (final concentration 1 $\mu$M) for determination of nonspecific binding, respectively. To assess the potency of various drugs in inhibiting specific binding, drugs are added (instead of buffer) to give 5 to 9 different concentrations between 1 nM and 10 $\mu$M, each in duplicate. After incubation for 15 min at 0° C., the assay mixtures are rapidly filtered through Whatman GF/B filters and washed twice with 5 ml of ice cold Tris-buffer. The filters are counted in Rialuma on a LKB Rach-Beta Liquid Scintillation Counter. $IC_{50}$ values (concentration of a test drug which inhibits specific binding of $^3$H-Flunitrazepam by 50%) are determined by linear regression analysis (HILL-Plot).

In other evaluations of benzodiazepine receptors involving the rat brain it is observed that the compounds of the formula I interact in a mode which differs from that of benzodiazepine in two different specific assays as follows:

1. In a Flunitrazepam Receptor Binding Assay as described by Speth et al., above, the compounds of the formula I exhibit—in contrast to classical benzodiazepines—a higher affinity for benzodiazepine receptors in cerebellum compared to hippocampus suggesting a more potent interaction with type I benzodiazepine receptors than with type II benzodiazepine receptors.

2. The compounds of formula I exhibit a differential interaction with benzodiazepine receptors after photoaffinity labelling with flunitrazepam when examined by the method described in Neuroscience Letters, 31 (1982), pages 65–69. In this assay conventional benzodiazepines exhibit after photoaffinity labelling with flunitrazepam when compared to untreated membranes a 20-fold and more increased $IC_{50}$ values after photoaffinity labelling whereas benzodiazepine antagonists exhibit unaltered $IC_{50}$ values. The compounds of formula I exhibit only up to 4-fold increased $IC_{50}$ values after photoaffinity labelling of benzodiazepine receptors when compared to the values obtained with control membranes. In addition, compounds of formula I exhibit increased affinity for benzodiazepine receptors of rat cerebral cortex in presence of 4-aminobutyric acid when compared to their respective affinity in the absence of 4-aminobutyric acid.

The mode of interaction of the compound of the formula I with benzodiazepine receptors therefore differs from that of conventional benzodiazepines and from that of benzodiazepine antagonists. The compounds of formula I possess a relatively high level of activity in the above indicated tests and possess an interesting and desirable spectrum of tranquilizer activity, particularly anti-anxiety activity. In addition, the compounds of formula I are indicated to have a stimulating effect on behavior in observation tests and to lack undesirable CNS depressant effects. For example, the compounds of the formula I are also indicated to be active in the well known hexobarbital reinduction test. However, at the doses at which the compounds are indicated to be useful as minor tranquillizers, e.g. by the FBA test and the conflict segment of the Geller Conflict test, the compounds I are generally indicated to be only weakly active or essentially inactive in a number of other standard CNS depressant tests, such as in sleep studies in monkeys, spinal reflex test in cats, the chemically induced convulsions test (in mice with N-sulfamoyl hexahydrol azepine), the Dunham rotarod test and, of further interest, in the variable interval segment of the Geller Conflict test. The compounds I are therefore indicated to have a very specific and desirable mode of action in effecting tranquillization, and in particular are indicated to effect tranquillization with a substantially reduced sedative action which is associated with, e.g. drowsiness, in most if not all of the currently available tranquilizers.

The compounds of the formula I exhibit a relatively high level of CNS depressant activity in the above-indicated FBA and Geller Conflict tests and possess an interesting and desirable spectrum of tranquilizer activity, more particularly anti-anxiety activity. For such use as tranquilizers, more particularly in the treatment of anxiety and/or tension, the amount of the compounds of the formula I to be administered will vary depending upon the compound used, mode of administration, the condition being treated, the severity of the condition and other known factors. However, in general satisfactory results are obtained when administered at a daily dosage of from 0.1 to 100 milligrams per kilogram of body weight, preferably given orally and in divided doses 2 to 4 times a day, or in sustained release form. For larger mammals the administration of from 10 to 500 milligrams per day provides satisfactory results and dosage forms for internal administration comprise from 2.5 to 250 milligrams of the compound in admixture with a solid or liquid carrier. The daily dosage for larger mammals is preferably from 10 to 200 milligrams and dosage forms preferably contain from 2.5 to 100 milligrams.

Pharmaceutical compositions provided by the invention and useful for effecting tranquilization of mammals contain a compound of the formula I as active ingredient and one or more conventional pharmaceutically acceptable carriers, including such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compositions of the invention adapted for oral or parenteral administration may contain from 1% to 90% by total weight of active ingredient in combination with the carrier, more usually 3% to 60%. The preferred unit dosage forms are the essentially solid forms adapted for oral administration.

A representative formulation for administering 3 to 4 times a day or as needed in treatment of anxiety and/or tension is a capsule prepared by conventional capsulating techniques and containing the following ingredients.

| Ingredient | Parts by Weight |
|---|---|
| 8-chloro-1-allyl-1,2,3,4-tetrahydro-6H-pyrimido[2,1-b]quinazolin-6-one | 10 |
| Lactose | 200 |

The generally preferred compounds of the formula I are those having at least one and preferably two or all of the following features: (a) R' being alkenyl, particularly allyl, cycloalkyl of 4 to 7 carbon atoms, particularly cyclohexyl, methyl substituted by cycloalkyl of 4 to 6 carbon atoms, particularly cyclohexylmethyl or norbornyl; (b) $R^o$ being H; (c) R being halo, particularly chloro, or trifluoromethyl, and (d) $R_1$, $R_2$ and $R_3$ all being H.

The following Examples illustrate compounds of the invention and their preparation.

EXAMPLE 1

1-allyl-7-chloro-2,3-dihydro-imidazo[2,1-b]quinazolin-5(1H)-one

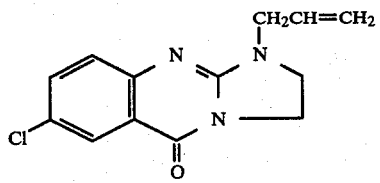

A solution of 1.0 g. of 3-(2-chloroethyl)-2,6-dichloro-3,4-dihydroquinazolin-4-one in 50 ml. of ethanol is combined with a solution of 0.62 g. of allylamine in 10 ml of dimethylacetamide and the resulting mixture heated to reflux with dimethylacetamide being added as required to dissolve any remaining solid starting material. After heating at reflux for about 5 hours the resulting reaction mixture is allowed to cool, the mixture stripped down to a dimethylacetamide slurry and pentane added. A white solid form which dissolves upon addition of water after which the organic layer is dried and concentrated in vacuo to a solid residue which is washed with pentane to obtain 1-allyl-7-chloro-2,3-dihydro-imidazo[2,1-b]quinazolin-5(1H)-one, m.p. 91°–93° C.

EXAMPLE 2

Following the procedure of Example 1 the following compound is prepared:
(A) 7-chloro-1-cyclopentyl-2,3-dihydro-imidazo[2,1-b]quinazolin-5(1H)-one, m.p. 142°–146° C.

The compounds of Examples 1 and 2 indicate an inhibition at 13% and 19% of control, respectively, compared to 44% of control for chlordiazepoxide in the Flunitrazepam Assay Test No. 1.

The 3-(2-chloroethyl)-2,6-dichloro-3,4-dihydroquinazolin-4-one is obtained by refluxing a solution of 17.3 g. of 4-(2-chloroethoxy)-2,6-dichloroquinazoline in 50 g. of trichlorobenzene for 3 hours and continuing the reflux for 2 more hours after washing the deposit in the tube back into the reaction mixture with methylene chloride. The resulting mixture is diluted with methylene chloride, filtered with carbon, the filtrate concentrated and chromatographed through silica gel by first adding in a minor portion of a 50:50 mixture of methylene chloride and pentane, eluding the trichlorobenzene spot with pure pentane and eluting the product out with methylene chloride which is then stripped off to a solid product, m.p. 161°–163° C.

EXAMPLE 3

Again following the procedure of Example 1 the following additional compounds are prepared on substitution of the appropriate corresponding starting materials:

(A) 7-chloro-1-cyclohexyl-2,3-dihydro-imidazo[2,1-b]quinazolin-5(1H)-one, m.p. 181°–183° C. (FBA test No. 1—11% of control)
(B) 7-chloro-1-cyclohexylmethyl-2,3-dihydro-imidazo[2,1-b]quinazolin-5-(1H)-one, m.p. 125°–127° C. (FBA test No. 1—8% of control)
(C) 7-chloro-1-cyclohepyl-2,3-dihydro-imidazo[2,1-b]quinazolin-5(1H)-one, m.p. 157°–159° C. (FBA test No. 1—27% of control)
(D) 7-chloro-1-cyclohexylmethyl-2-methyl-2,3-dihydro-imidazo[2,1-b]quinazolin-5(1H)-one, m.p. 152°–153° C. (FBA test No. 1—16% of control)
(E) 7-chloro-1-norbornyl-2,3-dihydro-imidazo[2,1-b]quinazolin-5(1H)-one, m.p. 155°–157° C. (FBA test No. 1—10% of control)
(F) 7-chloro-1-cyclooctyl-2,3-dihydro-imidazo[2,1-b]quinazolin-5-(1H)-one, m.p. 107°–110° C. (FBA test No. 1—39% of control)
(G) 8-chloro-1-allyl-1,2,3,4-tetrahydro-6H-pyrimido[2,1-b]quinazolin-6-one, m.p. 100°–102° C. (FBA test No. 1—4% of control)
(H) 8-chloro-1-cyclohexylmethyl-1,2,3,4-tetrahydro-6H-pyrimido[2,1-b]quinazolin-6-one, m.p. 120°–121° C. (FBA test No. 1—13% of control)
(I) 1-allyl-7-trifluoromethyl-2,3-dihydro-imidazo[2,1-b]quinazolin-5(1H)-one, m.p. 122°–124° C.
(J) 8-chloro-1-propargyl-1,2,3,4-tetrahydro-6H-pyrimido[2,1-b]quinazolin-6-one, m.p. 165°–167° C.
(K) 1allyl-7-trifluoromethyl-2,3-dihydro-imidazo[2,1-b]quinazolin-5(1H)-one, m.p. 122°–124° C.
(L) 8-chloro-1-cyclopentyl-1,2,3,4-tetrahydro-6H-pyrimido[2,1-b]quinazolin-6-one, m.p. 62°–65° C.
(M) 7-chloro-1-(3-fluoropropyl)-2,3-dihydro-imidazo[2,1-b]quinazolin-5(1H)-one, m.p. 120°–122° C. (FBA Test No. 1—15% of control).

What is claimed is:

1. A compound of the formula:

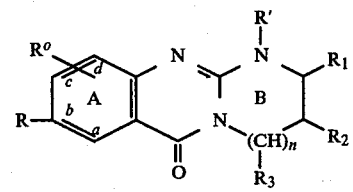

wherein
$R^o$ is hydrogen, halo of atomic weight of from 18 to 80, or alkyl of 1 to 3 carbon atoms,
R is halo of atomic weight of from 18 to 80, alkyl of 1 to 4 carbon atoms or trifluoromethyl,
R' is alkenyl of 3 to 6 carbon atoms, alkynyl of 3 to 6 carbon atoms, cycloalkyl of 3 to 8 carbon atoms, norbornyl, alkyl of 1 to 3 carbon atoms substituted by cycloalkyl of 3 to 7 carbon atoms or —CH$_2$(F$_x$-ALK) wherein
X is 1 to 3 and ALK is alkyl of 1 to 4 carbon atoms,
$R_1$, $R_2$ and $R_3$ are each independently hydrogen or alkyl of 1 or 2 carbon atoms, and n is 0 or 1,
or a pharmaceutically acceptable acid addition salt thereof.

2. A compound of claim 1 in which $R_1$, $R_2$ and $R_3$ are each H.
3. A compound of claim 2 in which $R^o$ is H.
4. A compound of claim 1 in which R is halo or trifluoromethyl.
5. A compound of claim 3 in which R is chloro or trifluoromethyl.
6. A compound of claim 1, 2, 3, 4 or 5 in which R' is alkenyl, cycloalkyl of 4 to 7 carbon atoms, methyl substituted by cycloalkyl of 4 to 6 carbon atoms or norbornyl.
7. A compound of claim 1, 2, 3, 4 or 5 in which R is allyl.
8. A compound of claim 6 in which n is 0.
9. A compound of claim 6 in which n is 1.

10. A compound of claim 1 in which n is 0.

11. A compound of claim 1 in which n is 1.

12. The compound of claim 1 which is 1-cyclohexyl-7-chloro-2,3-dihydro-imidazo[2,1-b]quinazolin-5(1H)-one.

13. The compound of claim 1 which is 1-cyclohexylmethyl-7-chloro-2,3-dihydro-imidazo[2,1-b]quinazolin-5(1H)-one.

14. The compound of claim 1 which is 1-allyl-8-chloro-1,2,3,4-tetrahydro-6H-pyrimido[2,1-b]quinazolin-6-one.

15. The method of tranquilizing a mammal comprising administering to a mammal a tranquilizing effective amount of a compound of claim 1.

16. The method of claim 15 in which $R_1$, $R_2$ and $R_3$ are each H.

17. The method of claim 16 in which $R^o$ is H.

18. The method of claim 15 in which R is halo or trifluoromethyl.

19. The method of claim 17 in which R is chloro or trifluoromethyl.

20. The method of claim 15, 16, 17, 18 or 19 in which R' is alkenyl, cycloalkyl of 4 to 7 carbon atoms, methyl substituted by cycloalkyl of 4 to 6 carbon atoms or norbornyl.

21. The method of claim 15, 16, 17, 18 or 19 in which R' is allyl.

22. The method of claim 20 in which n is 0.

23. The method of claim 20 in which n is 1.

24. The method of claim 15 in which n is 0.

25. The method of claim 15 in which n is 1.

26. The method of claim 15 in which the compound is 1-cyclohexyl-7-chloro-2,3-dihydro-imidazo[2,1-b]quinazolin-5(1H)-one.

27. The method of claim 15 in which the compound is 1-cyclohexylmethyl-7-chloro-2,3-dihydro-imidazo[2,1-b]quinazolin-5(1H)-one.

28. The method of claim 15 which the compound is 1-allyl-8-chloro-1,2,3,4-tetrahydro-6H-pyrimido[2,1-b]quinazolin-6-one.

29. A pharmaceutical composition comprising an inert pharmaceutically acceptable carrier and a tranquilizing effective amount of a compound of claim 1.

* * * * *